US012414513B2

(12) United States Patent
Dolcet Sanjuan et al.

(10) Patent No.: US 12,414,513 B2
(45) Date of Patent: Sep. 16, 2025

(54) REACTOR SYSTEM FOR IN VITRO CULTURE OF PLANT MATERIAL, KIT FOR TRANSFORMING A RECEPTACLE INTO A REACTOR SUITABLE FOR THE SYSTEM AND METHOD FOR IN VITRO CULTURE OF PLANT MATERIAL USING THE REACTOR SYSTEM

(71) Applicant: INSTITUT DE RECERCA I TECNOLOGIA AGROALIMENTÀRIES, Caldes de Montbui (ES)

(72) Inventors: Ramon J. Dolcet Sanjuan, Caldes de Montbui (ES); Carlos Rolando Mendoza Morales, Caldes de Montbui (ES)

(73) Assignee: INSTITUT DE RECERCA I TECNOLOGIA AGROALIMENTÀRIES, Caldes de Montbui (ES)

( * ) Notice: Subject to any disclaimer, the term of this patent is extended or adjusted under 35 U.S.C. 154(b) by 1047 days.

(21) Appl. No.: 17/297,721

(22) PCT Filed: Nov. 18, 2019

(86) PCT No.: PCT/ES2019/070787
§ 371 (c)(1),
(2) Date: May 27, 2021

(87) PCT Pub. No.: WO2020/109637
PCT Pub. Date: Jun. 4, 2020

(65) Prior Publication Data
US 2022/0022396 A1    Jan. 27, 2022

(30) Foreign Application Priority Data

Nov. 29, 2018   (ES) .................................. P201831164

(51) Int. Cl.
*A01H 4/00* (2006.01)
*C12M 1/00* (2006.01)
(Continued)

(52) U.S. Cl.
CPC .............. *A01H 4/001* (2013.01); *A01H 4/002* (2021.01); *A01H 4/005* (2013.01); *C12M 23/48* (2013.01);
(Continued)

(58) Field of Classification Search
CPC ........ A01H 4/001; A01H 4/002; A01H 4/005; C12M 23/48; C12M 29/10; C12M 23/08; C12M 25/14
See application file for complete search history.

(56) References Cited

U.S. PATENT DOCUMENTS 5,820,767 A  * 10/1998  Kane ...................... B01D 29/05
210/493.5

FOREIGN PATENT DOCUMENTS

| GB | 2533129   | 6/2016 |            |
|----|-----------|--------|------------|
| GB | 2533129 A | * 6/2016 | ............. A01G 22/00 |

(Continued)

OTHER PUBLICATIONS

International Search Report issued in PCT/ES2019/070787, mailed Jan. 16, 2020.

*Primary Examiner* — Liban M Hassan
(74) *Attorney, Agent, or Firm* — ICE MILLER LLP; Safet Metjahic

(57) ABSTRACT

It comprises a receptacle for the culture of plant material, a cap for closing an opening to said receptacle, and means for allowing the entry and/or exit of gas from said receptacle, and is characterized in that it comprises a container for receiving a liquid culture medium inside the receptacle, and support means for supporting the plant material on said (Continued)

reception container, wherein said container is attached to the lid of the receptacle in a position suitable for use, said lid including at least one medium inlet and/or exit conduit that connects with the container to be able to fill and/or empty said container through said conduit.

16 Claims, 6 Drawing Sheets

(51) Int. Cl.
*C12M 3/00* (2006.01)
*C12M 1/12* (2006.01)
*C12M 1/24* (2006.01)

(52) U.S. Cl.
CPC ............ *C12M 29/10* (2013.01); *C12M 23/08* (2013.01); *C12M 25/14* (2013.01)

(56) References Cited

FOREIGN PATENT DOCUMENTS

| | | |
|---|---|---|
| MX | 2016015393 | 5/2018 |
| WO | 2012044239 | 4/2012 |
| WO | 2012156440 | 11/2012 |
| WO | 2014072962 | 5/2014 |

* cited by examiner

REACTOR SYSTEM FOR IN VITRO CULTURE OF PLANT MATERIAL, KIT FOR TRANSFORMING A RECEPTACLE INTO A REACTOR SUITABLE FOR THE SYSTEM AND METHOD FOR IN VITRO CULTURE OF PLANT MATERIAL USING THE REACTOR SYSTEM

CROSS-REFERENCE TO RELATED PATENT APPLICATIONS

This is a U.S. National Phase Application under 35 U.S.C. § 371 of International Patent Application No. PCT/ES2019/070787, filed Nov. 18, 2019, and claims priority to Spanish Patent Application No. P201831164, filed Nov. 29, 2018, which is incorporated by reference in its entirety. The International Application was published on Jun. 4, 2020, as International Publication No. 2020/109637 Al.

The present invention relates to a reactor system for clonal propagation of plants comprising a receptacle for in vitro culture of plant material. It also relates to a kit suitable for converting a receptacle into an in vitro culture reactor of plant material suitable for said system, and to a method for in vitro culture of plant material by said reactor system.

BACKGROUND OF THE INVENTION

Reactor systems for in vitro culture of plant material are known, such as Plantform® or Rita® brand reactor systems, comprising a receptacle provided with a tray for supporting the plant material, a lid for closing an opening to the receptacle and a number of air injection conduits with which temporary pumping of a liquid culture medium stored at the bottom of the culture receptacle is achieved. The system of temporary immersion of the plant material in a liquid culture medium has the advantage over other in vitro culture systems in that it provides a uniform distribution of nutrients, which results in faster growth of the plant material and an increase in the quality of the material obtained.

Plantform® or Rita® reactor systems have the advantage that they take up little space, making them easy to place and store in the in vitro culture chambers. However, these reactor systems have the disadvantage that the liquid culture medium remains in contact with the receptacle during culture, making it difficult to change the medium, as well as to handle the reactor to comfortably access the plant material during the cutting and harvesting phase.

There are other reactor systems, such as the Setis® brand reactor systems, which include two separate receptacles with their respective lids connecting with each other. A first receptacle is employed for growing plant material while a second receptacle is employed for storing the liquid culture medium, which is periodically pumped through a connector to the first receptacle to carry out temporary immersion of the plant material in the culture medium. The first receptacle in which the plant material is housed is stacked over the second receptacle and includes an inclined bottom to facilitate drainage of the liquid culture medium.

The Setis® reactor system has the advantage that it facilitates changing the medium during the growth phase of the plant material given that it has a separate receptacle that can be disconnected to sterilize and replace the liquid culture medium that is housed inside. However, this reactor system has the disadvantage of taking up space in the in vitro culture chambers. In addition, the presence of two receptacles makes it difficult to manage the system, and in particular, to access the plant material for cutting and harvesting.

DESCRIPTION OF THE INVENTION

The object of the present invention is to provide a reactor system for in vitro culture of plant material that solves the aforementioned drawbacks, presenting the advantages that will be described below.

In accordance with this object, according to a first aspect, the present invention provides a reactor system for the in vitro culture of plant material, comprising a receptacle for the culture of plant material, a lid adapted to closing an opening of said receptacle, and means for allowing the entry and/or exit of gas from said receptacle.

The system is characterized in that it comprises a container for receiving a liquid culture medium inside the receptacle and support means for supporting the plant material on said receiving container, wherein said container is attached to the lid of the receptacle in a position suitable for use, said lid including at least one medium inlet and/or outlet conduit communicating with the container to be able to fill and/or empty said container through said conduit.

In the claimed reactor system, the culture medium is pumped from the outside through a conduit that communicates the lid with the container receiving the liquid medium and in turn supports the plant material. This container is preferably attached to the lid of the culture receptacle in a position suitable for use, so that when the lid is removed, the container on which the plant material is supported is simultaneously removed. As a result, access to plant material for cutting or harvesting is very convenient and easy.

Another advantage of the claimed system lies in the fact that the culture medium never comes into contact with the culture receptacle, since the inlet and outlet of the medium occurs through at least one conduit that directly communicates the lid with the media receiving container. Thanks to this, the dimensions of the culture receptacle can be reduced, and in addition, the shape and size of the receptacle can be very varied, with the sole condition that the dimensions of the opening always make it feasible to introduce the container attached to the lid in a position suitable for use. In fact, in the claimed system, the receptacle may be, for example, a conventional receptacle made of glass, or other material, of the type commercially available for multiple uses, and including, for example, a threaded opening capable of being closed and sealed by a system lid adapted with a complementary thread.

According to a second aspect, the present invention provides a conversion kit for converting a receptacle into a reactor for in vitro culture of plant material, characterized in that it comprises;
a) a lid adapted to close an opening of said receptacle,
b) a liquid culture medium receiving container for receiving a liquid culture medium within the receptacle, said container being attached to the lid of the receptacle in a position suitable for use, and said lid including at least one culture medium inlet and/or outlet conduit communicating with the container so as to be able to fill and/or empty said container through said conduit, and
c) support means for supporting the plant material on said culture medium receiving container.

The present invention provides a kit for converting a receptacle, for example, a commercial receptacle of various shapes, dimensions and materials, into a reactor for the in vitro culture of plant material suitable for the claimed system. This reactor can be used to grow in vitro plant material for industrial, research or household food use. For example, the kit may be used to convert a conventional receptacle into a reactor that allows the in vitro culture of soybeans whose sprouts may have a commercial or domestic food-type use.

In particular, the kit provides a lid adapted to close the opening of a receptacle. This lid may be, for example, a lid provided with a thread and adapted to close and seal an opening of a conventional receptacle, for example, a conventional glass receptacle, or other material, of the type commercially available for multiple uses.

The lid of the kit has the particular feature that it is attached to a container for the reception of a liquid culture medium on which the plant material is supported in a position suitable for use, so that the opening of the receptacle must allow the passage of this container in order to be able to attach the lid. By removing the same lid or receptacle, the receiving container including the culture medium and plant material is removed or accessed, leaving the culture receptacle free and intact. The filling of the receiving container takes place through a conduit provided in the lid itself to feed the culture medium from an outer reservoir.

According to one embodiment, the culture medium receiving container is attached to the lid such that in a position suitable for use it extends longitudinally into the culture receptacle from an inner face of the lid body. For example, the container may extend longitudinally within the culture receptacle attached to the lid such that it does not contact the walls of this receptacle. Thanks to these characteristics, unlike state-of-the-art reactor systems, the claimed reactor system allows working with lower volumes of culture medium, saving costs and space.

Preferably, according to a preferred embodiment, the lid body comprises a support base configured to be able to maintain the receptacle and the liquid culture medium receiving container in a stable horizontal position, when the receptacle is attached to the lid.

This particular lid configuration has the advantage of maximizing the useful culture surface of the culture medium receiving container, which extends longitudinally attached to the lid in a horizontal position inside the receptacle. As a result, this makes it possible to grow a large number of units of plant material in a very convenient way. Another advantage lies in the fact that the technician can manipulate the plant material by keeping the container and lid assembly in a stable horizontal position.

Advantageously, the end of the receiving container attached to the inner face of the lid includes raised side walls adapted to get in contact with the opening of the receptacle. These side walls are coupled to the opening of the receptacle and have the function of preventing the plant material from falling out of the receptacle, or preventing the plant material from coming into contact with the external parts of the receptacle, or with the hands of a technician at the time of plant material extraction.

Again advantageously, the culture medium receiving container includes a cavity provided with an orifice for actively or passively draining the liquid culture medium to the outlet and/or inlet conduit of the lid. Optionally, the inner bottom of the receiving container may be configured with a slope to facilitate drainage of the liquid to the outlet orifice. This orifice can be used to inject the liquid culture medium through a tube associated with an outer reservoir in which said culture medium is stored.

Preferably, the lid of the receptacle comprises at least one orifice for the inlet and/or outlet of gas from the receptacle. A gas may be injected through this orifice to modify the inner atmosphere of the receptacle, if necessary.

Again preferably, the plant material support means comprises at least one body, for example a platform shaped body, adapted to be removably attached to the container receiving the liquid culture medium, said body being configured to allow contact of the liquid culture medium with the plant material.

According to one embodiment, the body on which the plant material is supported comprises a support platform provided with a number of perforations to allow passage of an upflow of liquid culture medium. This platform is adapted to be removably anchored inside the container, maintaining a predetermined distance from the bottom of the same container.

According to a different embodiment, instead of a platform, the body supporting the plant material and allowing the passage of liquid may be configured, for example, as a tissue, such as a porous tissue, or a permeable membrane, or inert material allowing the passage of liquid. This body shall be arranged on the receiving container of the culture medium.

Advantageously, the system comprises fastening means for fastening the plant material capable of growing on the receiving container of the culture medium. These fastening means are removably attached on the receiving container, or more specifically, on the support platform that is anchored to the culture medium receiving container, to allow the passage of the shoots or growing parts of the plant material.

Preferably, the fastening means are configured as a grid, so that the frame of this grid fastens the base of the plant material that grows on the receiving container or, more specifically, on the support platform of said plant material.

The supporting of the plant material by means of a grid, or any other similar or equivalent means, facilitates the cutting and collection of shoots, since it keeps the explants in position, without the need to manually manipulate them, when the receiving container tilts or inverts held by the lid to facilitate the cutting and collection operations of the plant material. When these operations are performed, the container cavity is free of liquid culture medium, since the medium has been previously drained through the lid liquid outlet conduit.

Again preferably, the claimed reactor system comprises pumping means for pumping at a predetermined frequency the liquid culture medium through the at least one culture medium inlet and/or outlet conduit of the lid, said pumping making it possible to temporarily immerse the plant material disposed on the support means of the culture medium receiving container.

According to a third aspect, the present invention provides a method for culturing plant material in vitro in a receptacle by the claimed reactor system, comprising the steps of:
 a) injecting a liquid culture medium into the culture receptacle through at least one inlet conduit provided in a lid attached to a culture medium receiving container,
 b) maintaining temporarily immersed in the liquid culture medium a plant material previously deposited on the receiving container that is attached to the lid,
 c) actively or passively draining the liquid culture medium through an outlet conduit provided in the lid,
 d) after step c), accessing the culture medium receiving container and the plant material assembly deposited on the container, to carry out cutting and harvesting on the outside of the receptacle.

The claimed in vitro culture method has the advantage of obtaining a higher rate of multiplication of the plant material, since the shoots are longer, of greater fresh weight and with larger leaves than those obtained with other culture methods. This is due to the fact that the reactor system allows for an optimal frequency of temporary immersion in the liquid medium, while also guaranteeing optimal drainage of the medium through the outlet conduit provided in the lid, which communicates directly with the drainage orifice of the container itself.

Furthermore, the claimed method allows access to the plant material in a very easy manner, by removing the lid or receptacle to access the receiving container and the plant material supported on the receiving container. Once outside the receptacle, the container may be inverted, or tilted, to facilitate the cutting and harvesting of the plant material. In addition, for embodiments in which the lid is provided with a support base configured to maintain the container itself in a stable horizontal position, handling of the plant material is extremely easy.

Optionally, the claimed method comprises the step of modifying the interior atmosphere of the culture receptacle by injecting gas through at least one lid conduit communicating with the interior of the receptacle.

In the present invention;

Plant material means any type of material capable of growing, or of being vegetatively multiplied or propagated, for example, a material containing or consisting of plant tissues, plant organs, seeds and/or plant cells, preferably said material may consist of explants or living tissues isolated from its own organ, prepared aseptically.

Culture receptacle means a container in which the growth of the plant material is carried out.

In vitro culture means a culture of plant material for industrial use, research use, commercial food use or domestic use, capable of being carried out by the claimed system either in industrial facilities, research laboratories, commercial premises, or in the home of a user. In vitro culture comprises plant material, such as explants or parts of a plant or seed, and it is carried out under controlled temperature, photoperiod and light intensity conditions, with culture media formulated based on predetermined targets. Optionally, the plant material may comprise biotic agents, for example bacteria and/or fungi, or abiotic agents, for example chemical compounds added to the liquid culture medium.

BRIEF DESCRIPTION OF THE DRAWINGS

For a better understanding of what has been stated, some drawings are attached in which, schematically and only by way of non-limiting example, a practical case of realization is represented.

DESCRIPTION OF A PREFERRED EMBODIMENT

A preferred embodiment of the system and kit of the present invention is described below with reference to FIGS. 1 to 7.

Figure 1:
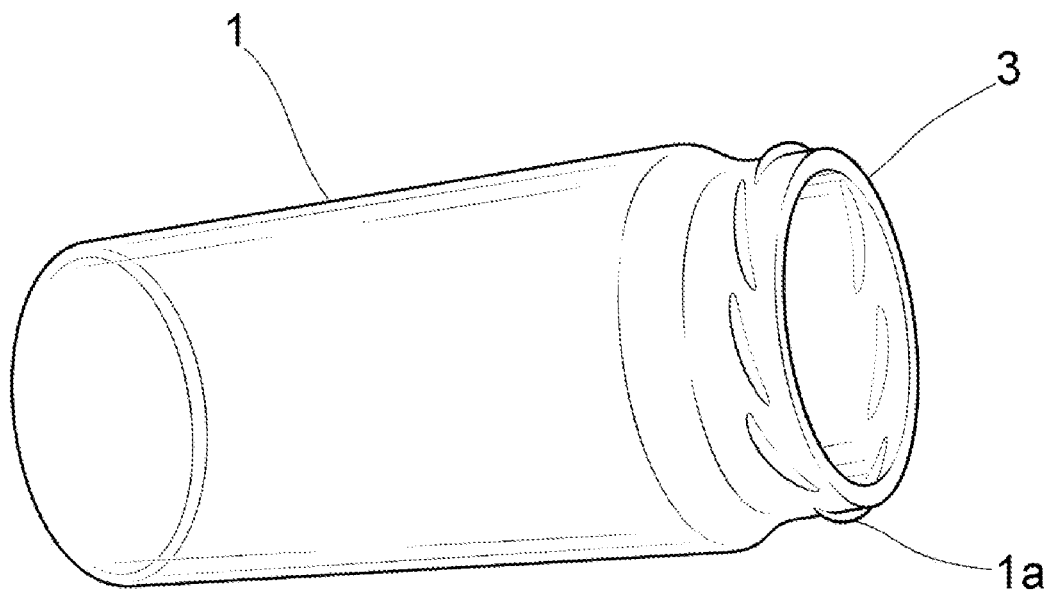
FIG. 1 is a perspective view of an embodiment of the culture receptacle of the reactor system of the present invention.

As discussed in the preceding sections, the present invention provides a reactor system and a conversion kit suitable for converting a conventional receptacle 1, as shown in FIG. 1, into a reactor for the in vitro culture of plant material.

In the embodiment described, the kit consists of the following components;

- a lid 2 for closing the receptacle 1 where the culture is carried out,
- a container 4 receiving the liquid culture medium (not shown) that is attached to the lid 2,
- a platform shaped body 6 with perforations 6a that allows the plant material 11 to be supported on the container 4,
- a body 7 in the form of a grid that can be removably attached to the body 6 or support platform, in order to fasten the base of the plant material 11 and facilitate the cutting and harvesting of the shoots of said plant material 11,
- a conduit 5 for the inlet and/or outlet of the liquid culture medium through the lid 2, and
- two orifices 8, 9 for the inlet and/or outlet of gases from the culture receptacle 1.

The lid 2 can be, for example, a lid 2 provided with a thread 2a and adapted to close and seal by threading 1a the opening 3 of the conventional receptacle 1, which in the embodiment described is a commercially available, multi-purpose receptacle 1 made of glass or polycarbonate. A sealing gasket 10 is attached to the cover 2 to ensure the sealing of the assembly.

The reactor system includes means (not shown) for pumping liquid culture medium from an external reservoir (not shown) to the receiving container 4 at a predetermined frequency.

In the embodiment described, the lid 2 has the peculiarity that it includes a support base 2b configured to be able to maintain the receptacle 1 and the culture medium receiving container 4 in a stable horizontal position. As can be seen in FIGS. 4 to 7, the culture medium receiving container 4 extends longitudinally integrally attached to the lid 2, from an inner face of said lid 2, so that it is arranged in a stable horizontal position, substantially parallel to the walls of the culture receptacle 1 a, but without contacting these walls.

As discussed in the description of the invention, this particular configuration allows the maximization of the useful culture area and also working with lower volumes of culture medium, saving cost and space.

Figure 4:
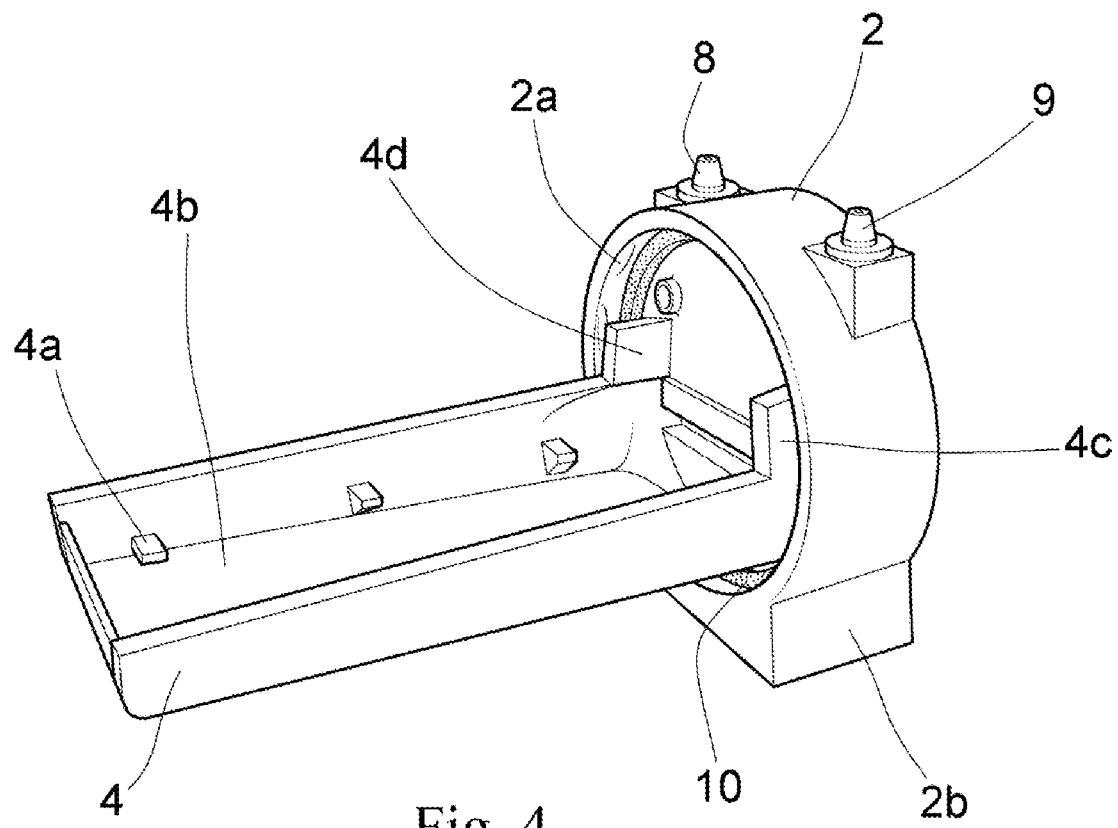
FIG. 4 is a perspective view of a lid and liquid culture medium receiving container assembly, which is attached to the lid by its inner face. This lid is adapted to close the opening of the receptacle in FIG. 1.

FIG. 4 shows a perspective view of the assembly of lid 2 and receiving container attached to the lid 2. In this figure, it is possible to see the inclined bottom 4b for the active or passive drainage of the culture medium through an orifice that connects with the lid 2 and the liquid culture medium outlet conduit 5. The side walls of the container 4 include protrusions 4a that serve as a support base for the body 6 or platform on which the plant material is supported. These protrusions 4a are positioned at half height on the walls of the container 4, so that the body 6 or platform on which the explants are arranged can be flooded with liquid medium when the culture medium passes through the perforations 6a (see FIG. 3).

Continuing with the description of FIG. 4, it can be seen that the container 4 includes at the end that contacts the inner face of the lid 2, some raised walls 4d adapted to fit into the walls of the opening 3. Hence, spillage of liquid medium is avoided when the technician slightly tilts the reactor, or the lid 2 and receiving container 4 assembly, to carry out the cutting of the plant material.

Figure 2:
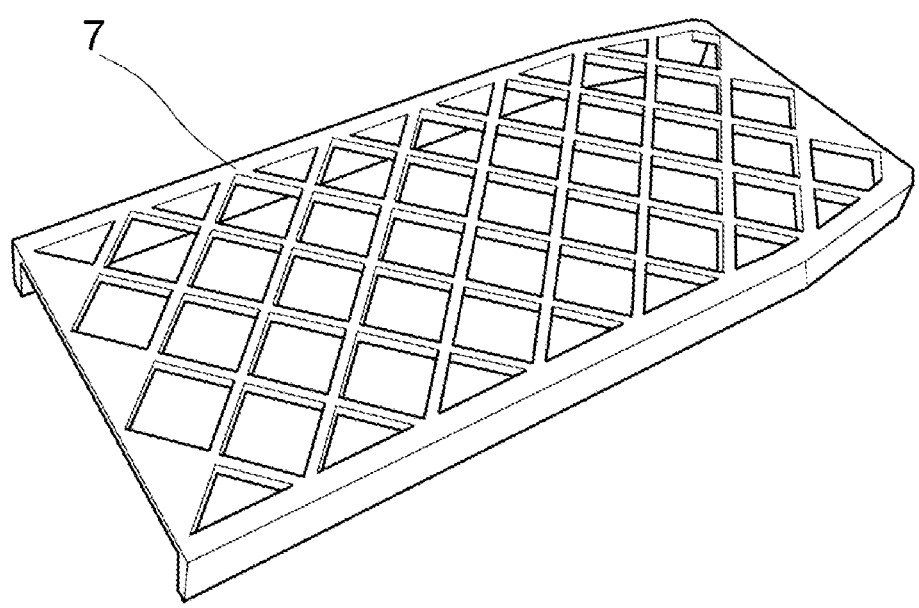
FIG. 2 is a perspective view of a fastening means for fastening the plant material in the form of a grid forming a lattice.
Figure 3:
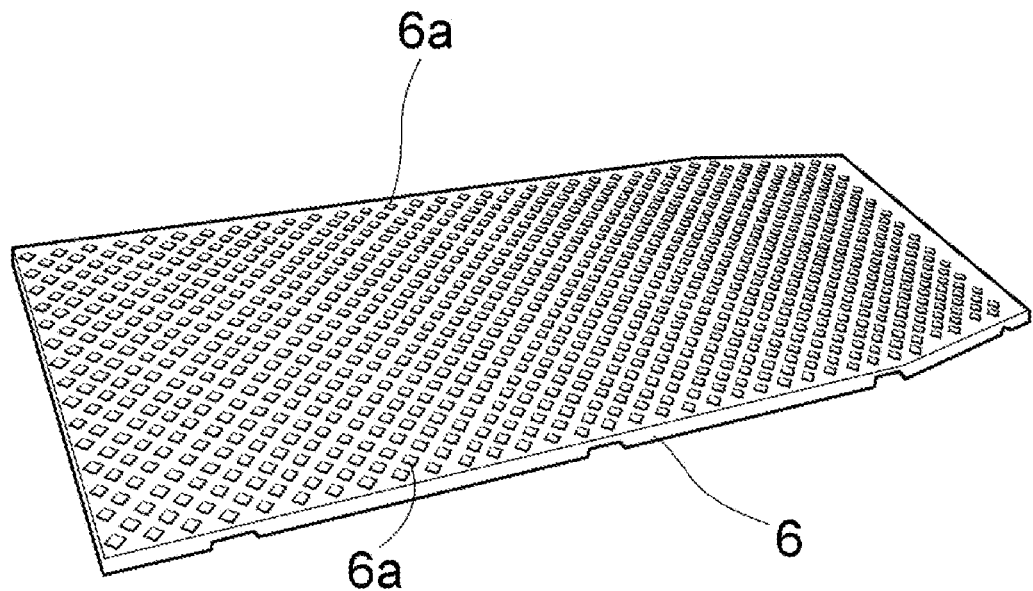
FIG. 3 is a perspective view of some support means for supporting plant material on the culture medium receiving container, which are configured as a platform provided with a number of perforations to allow upflow of the liquid culture medium.
Figure 6:
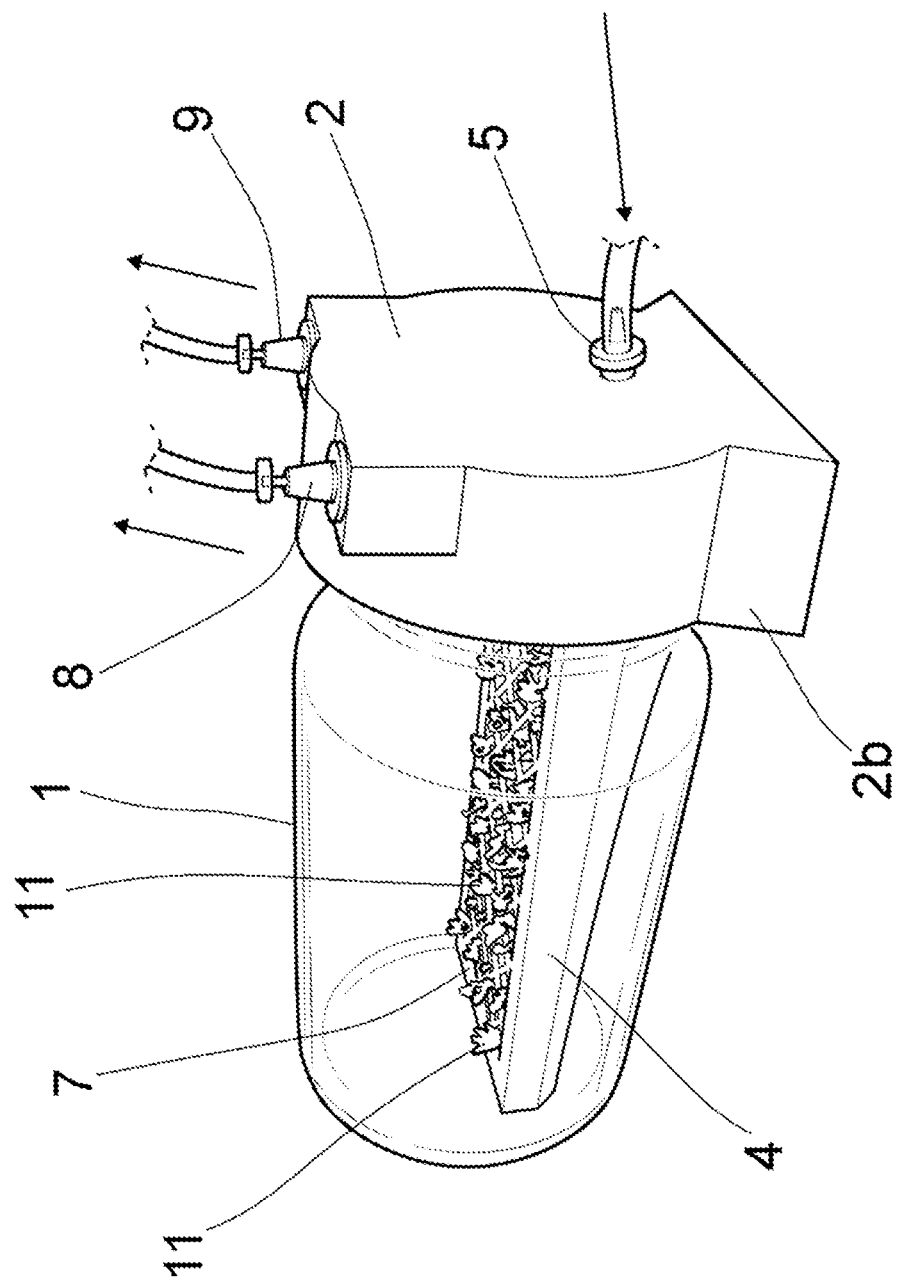
FIG. 6 is a perspective view showing the reactor system in the culture phase, when the culture medium receiving container is fed from the outside through a conduit provided in the lid to perform temporary immersion of the plant material. The arrows indicate the entry of the liquid medium that causes the simultaneous exit of air from inside the culture receptacle.
Figure 7:
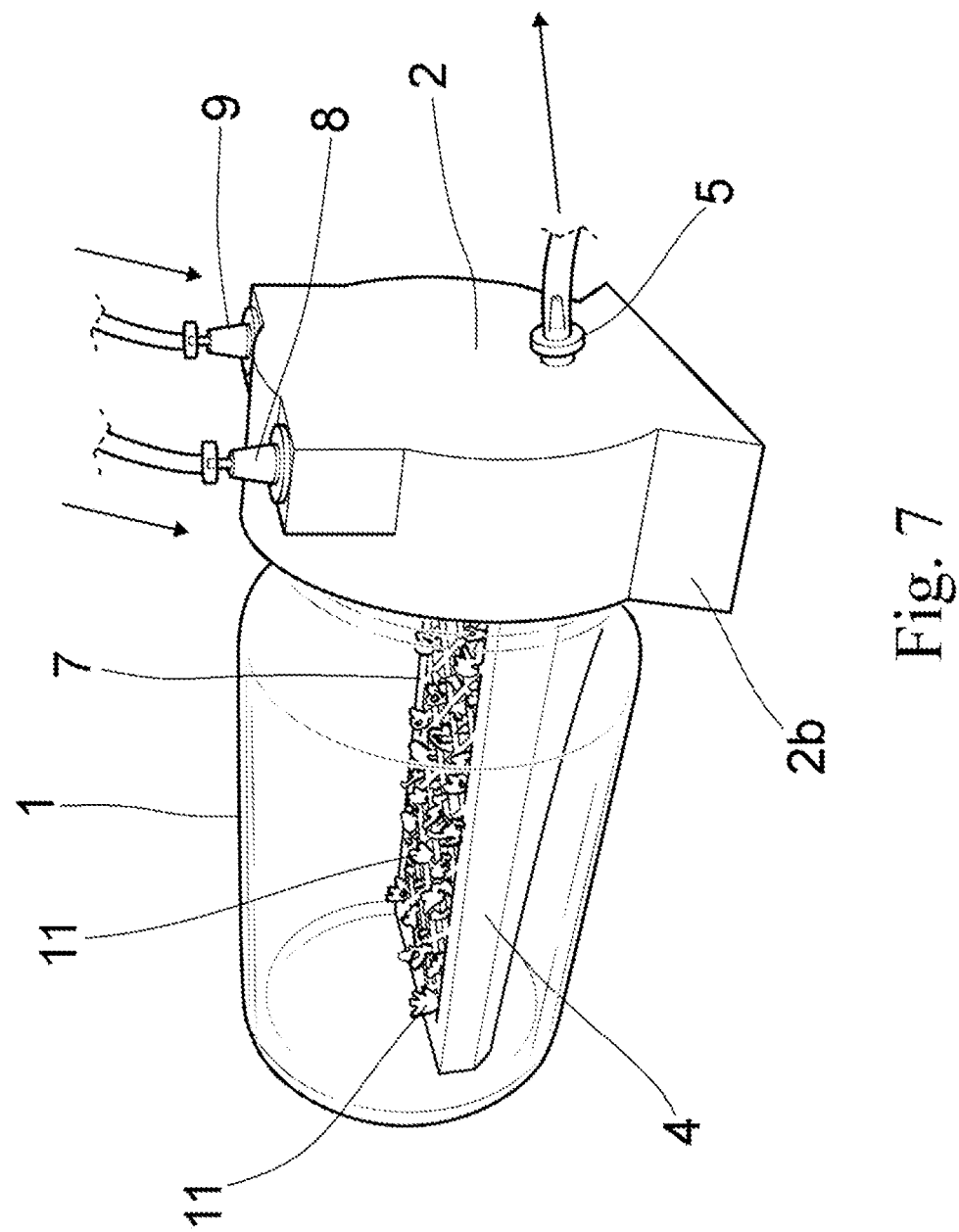
FIG. 7 is a perspective view showing the reactor system in culture phase, when the liquid culture medium leaves the container through the lid conduit. The arrows indicate the outlet of the liquid medium that causes the simultaneous entry of air into the culture receptacle.

FIG. 2 shows a perspective view of the grid-like body 7, provided with a lattice that is traversed by the shoots of the plant material 11 (see FIGS. 6 and 7). This lattice serves to fasten the base of the explants when the container 4 is tilted to facilitate rapid cutting and harvesting of the shoots. This grid or body 7 includes side walls 7a that are arranged on the support platform or body 6, at a certain distance from said platform.

As discussed in the description of the invention, unlike state-of-the-art reactor systems, the reactor system of the present invention has the advantage that the collection or cutting of shoots is carried out by accessing the lid 2 and receiving container 4 assembly from the outside of the receptacle 1, so that the technician can even slightly tilt this assembly to facilitate rapid cutting of the plant material 11 in different positions.

Below, it follows a description of the in vitro culture method of plant material 11 in the reactor system claimed and described in the accompanying figures.

Figure 5:
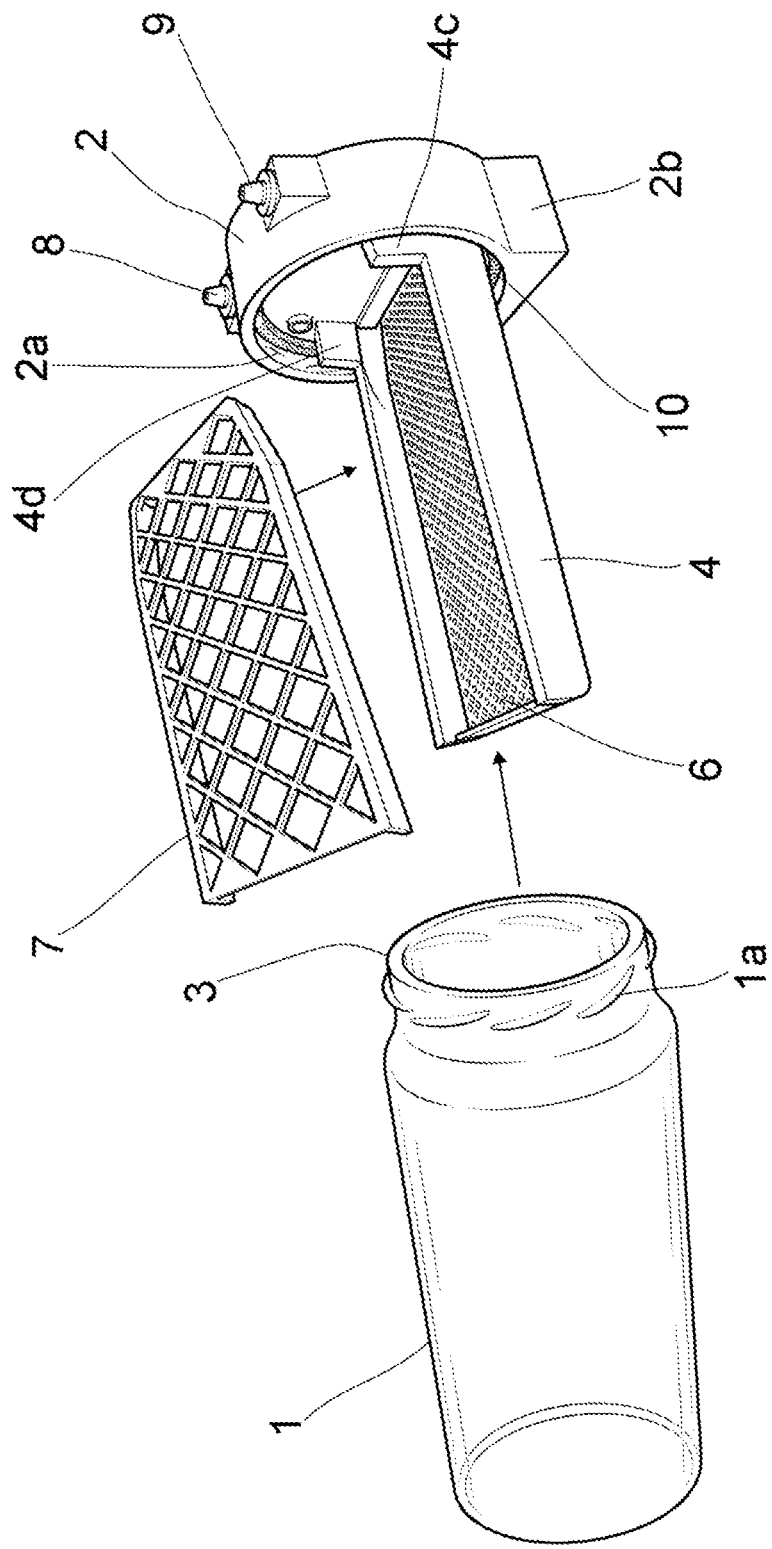
FIG. 5 is an exploded perspective view schematically depicting the assembly of the reactor system with the claimed kit.

Once the different components have been assembled following the arrangement shown schematically in FIG. 5, air filters (not shown) are connected to the gas inlet and outlet orifices 8 and 9 of the lid 2, and a tube is connected to the inlet and outlet conduit 5 of liquid culture medium. The assembly is sterilized before being used for explant culture in order to ensure sterile conditions.

After sterilization, the container 4 and lid 2 assembly is accessed inside a laminar flow cabinet and, under sterile conditions, the plant material 11 is deposited on the platform or body 6 taking advantage of the openings left by the frame of the body 7 or grid fastening the explants.

Once the plant material 11 has been deposited, the container 4 and lid 2 assembly is introduced into the culture receptacle 1 and arranged in an in vitro culture chamber, under controlled temperature, photoperiod and light intensity conditions. The liquid culture medium is then injected into the interior of the receptacle 1 through the inlet conduit 5 provided in the lid 2 until the plant material 11 is immersed in the medium. The injection is carried out periodically from an external tank (not represented) through pumping means, using timers.

During culture, the plant material 11 is temporarily immersed in accordance with the temporary immersion culture system, already known in the state of the art. The immersion phase is short, a few minutes, to moisten the explants, leaving them impregnated with culture medium. When the injection stops, the medium is drained from the inclined bottom 4b through the same conduit 5 of the lid 2 acting at this time as the outlet conduit (see FIG. 7). During the injection, the air inside the receptacle 1 exits through the orifices 8, 9 provided in the lid 2 and associated with the filters (not shown) (see FIG. 6). However, when stopping the injection and draining the medium, new air enters through the same orifices 8 and 9. If necessary, the inner atmosphere of culture receptacle 1 may be modified by injecting a gas.

The plant material 11 remains impregnated with medium for hours, growing inside the culture receptacle 1 under controlled light and temperature conditions. When it is necessary to cut or collect the plant material, the technician accesses the container 4 and lid 2 assembly, unscrewing in this case the receptacle 1. The support base 2b of the lid 2 allows the container 4 to be held in a stable horizontal position for accurate cutting.

As mentioned in the description of the invention, the culture method described allows a higher multiplication rate of the plant material 11 to be obtained, with longer shoots, higher fresh weight and larger leaves than those obtained with other culture methods using other reactor systems.

The table below shows the results from a culture test performed using a Rita® brand reactor system and the claimed reactor system.

| In vitro culture type | Number of initial explants per receptacle | No. of new shoots obtained/ receptacle | Multiplication Rate No. of Shoots Obtained/ Initial Explants | Average length of shoots (mm) | Fresh weight per shoot (g) |
|---|---|---|---|---|---|
| With liquid medium by means of a RITA ® reactor | 15 | 70-100 | 5 | 20 | 0.5 |
| With liquid medium by means of the reactor system of the present invention | 80 | 400-700 | 8 | 40 | 0.7 |

The results show that the number of initial explants per culture receptacle is much higher in the reactor system of the present invention. The number of final shoots obtained and the average length and weight of the shoots are also higher.

Although reference has been made to a particular embodiment of the invention, it is apparent to an expert in the field that the disclosed reactor and kit system is susceptible to numerous variations and modifications, and that all of the aforementioned details may be replaced by other technically equivalent details, without departing from the scope of protection defined by the appended claims. For example, although an embodiment has been described in which the lid 2 includes a support base 2b and the receptacle 1 is of the conventional type, the same reactor system would be feasible with a receptacle that includes a support base that would also allow the assembly to be held in a stable horizontal position. In this case, it would not be necessary for the lid to have a support base, and the lid and container assembly could also be removed to perform cutting and collection, although, once removed from the receptacle, it could not by itself be kept in a stable horizontal position. Similarly, although means for supporting and fastening the plant material 11 in the form of a platform and grid have been described, similar results could be obtained with other means for supporting and fastening the plant material, provided that these means allow the plant material to also be impregnated by the culture medium stored in the cavity of the container 4 attached to the lid 2.

The invention claimed is:

1. A reactor system for in vitro culture of plant material, the system comprising:
    a culture container arranged to hold a plant material;
    a culture receptacle having an opening arranged to receive the culture container;
    a lid attached to the culture container and arranged to close the opening to said culture receptacle with the culture container in the culture receptacle; and
    at least one gas orifice arranged to allow entry or exit of a gas in said culture receptacle,
    wherein the culture container includes
        a cavity arranged for receiving and holding a liquid culture medium without contacting the culture receptacle, and
        a support unit arranged to hold the plant material, and
    wherein said lid includes at least one conduit in fluid communication with the culture container to fill or empty said culture container without the liquid culture medium contacting the culture receptacle.

2. The reactor system according to claim 1, wherein the culture container is attached to the lid and extends longitudinally from one face of the lid.

3. The reactor system according to claim 1, wherein the lid comprises a support base configured to maintain the culture receptacle and the culture container in a stable horizontal position.

4. The reactor system according to claim 2, wherein an end of said culture container includes raised side walls configured to contact a portion of the culture receptacle at the opening and facilitate cutting of the plant material without damaging the lid.

5. The reactor system according to claim 1, wherein said cavity is provided with an inclined bottom and an orifice for draining the liquid culture medium to the at least one conduit.

6. The reactor system according to claim 1, wherein said support unit comprises at least one supporting body configured for being removably attached to the culture container, said supporting body being configured to allow contact of the liquid culture medium with the plant material.

7. The reactor system according to claim 1, further comprising a fastener body configured to fasten the plant material on said support unit.

8. The reactor system according to claim 7, wherein said fastener body comprises a grid with a lattice configured to fasten to the plant material.

9. The reactor systemSystem according to claim 1, wherein said at least one gas orifice comprises at least one orifice provided in the lid.

10. The reactor system according to claim 1, wherein said opening is sized to allow introduction of the culture container into the culture receptacle.

11. The reactor system according to claim 1, wherein the opening includes a thread and said lid is configured for closing and sealing said opening, said lid comprising a support base configured to maintain the culture receptacle and the culture container in a stable horizontal position while said culture receptacle is coupled to the lid.

12. The reactor system according to claim 1, further comprising a pumping device for pumping at a predetermined frequency the liquid culture medium through said at least one conduit and temporarily immerse the plant material in the liquid culture medium.

13. A method for culturing in vitro plant material by the reactor system according to claim 1, the method comprising:
    a) injecting a liquid culture medium into the culture receptacle through the at least one conduit provided in the lid attached to a culture container, which is configured for receiving the liquid culture medium;
    b) maintaining temporarily immersed in the liquid culture medium a plant material previously deposited on the culture container;
    c) actively or passively draining the liquid culture medium through the at least one conduit; and
    d) after step c), accessing the culture container attached to the lid to perform cutting and collecting of the plant material from outside the culture receptacle.

14. The method according to claim 13, further comprising modifying the interior atmosphere of the culture receptacle by injecting a gas through the at least one gas orifice.

15. The method according to claim 13, wherein the lid includes a support base adapted to maintain the culture receptacle and the culture container in a stable horizontal position while said culture receptacle remains attached to the lid.

16. A reactor system for in vitro culture of plant material, comprising:
    a culture receptacle made and arranged for a plant material,
    a lid made and arranged for closing an opening to said culture receptacle;
    a gas inlet and/or outlet means for allowing the entry and/or exit of gas from said culture receptacle;
    a culture receiving container including a cavity made and arranged for receiving a liquid culture medium inside the culture receptacle without the culture medium coming into contact with the culture receptacle; and
    a plant support unit for supporting the plant material on said culture receiving container,
    wherein said culture receiving container is attached to the lid of the culture receptacle in a position suitable for use, said lid including at least one inlet and/or outlet conduit arranged to communicate with the cavity of the culture receiving container, to be able to fill and/or empty the cavity of said culture receiving container through said conduit without the culture medium coming into contact with the culture receptacle, and
    wherein said culture medium receiving container includes said cavity provided with an inclined bottom and an orifice for draining the liquid culture medium to the at least one inlet and/or outlet conduit.

* * * * *